United States Patent [19]

Pedersen et al.

[11] Patent Number: 4,677,238

[45] Date of Patent: Jun. 30, 1987

[54] PREPARATION OF INDENES

[75] Inventors: S. Erik Pedersen, Solon; Linda L. Pfingsten, Columbia Station, both of Ohio

[73] Assignee: The Standard Oil Company, Cleveland, Ohio

[21] Appl. No.: 906,851

[22] Filed: Sep. 12, 1986

[51] Int. Cl.⁴ .................. C07C 1/20; C07C 11/253
[52] U.S. Cl. .............................. 585/469; 585/409
[58] Field of Search ........................ 585/409, 469

[56] References Cited

U.S. PATENT DOCUMENTS 4,568,782 2/1986 Pagnotta et al. .................. 585/409

Primary Examiner—Curtis R. Davis
Attorney, Agent, or Firm—Charles S. Lynch; John E. Miller; Larry W. Evans

[57] ABSTRACT

Disclosed is the vapor phase cyclodehydration of an aldehyde or ketone over a solid catalyst which comprises phosphoric acid on a solid inorganic oxide support to make indene or a substituted indene according to the equation:

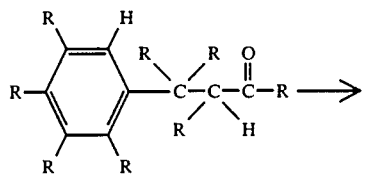

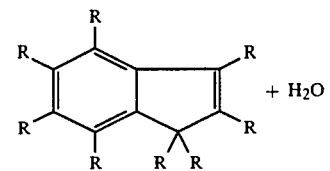

10 Claims, No Drawings

PREPARATION OF INDENES

The present invention relates to the preparation of indene or substituted indenes by the vapor phase catalytic reaction involving cyclodehydration of 3-phenylpropionaldehydes and 3-phenylpropylketones.

Indenes are currently prepared industrially by isolation from coal tar or petroleum distillates. This method yields indene of too low a purity to be useful for preparation of high HDT polymers without extensive and costly purification. High purity indene is not currently an item of commerce in more than research quantities. Syntheses of indene have traditionally relied upon cumbersome, multi-step, non-catalytic methods which are not industrially useful because of their inherently low yields and poor product recovery as well as their requirement of highly acidic reaction conditions (see, for example, Wittig, G. *Chem. Ber.* 91, 1958, 895 or Waldman and Schwenk, *Ann.* 487, 1931, 287; or Ulman and Lehner, *Ber.* 38, 1905, 729; or Weedon and Wahler, *J. Am. Chem. Soc.* 33, 1905, 386.

It is an object of the present invention to provide a process for making indenes synthetically.

It is a further object to provide a one step process for making indenes from relatively inexpensive starting materials in a single reaction step.

Other objects, as well as aspect, features, and advantages, of the invention will be apparent from the disclosure and claims.

These and other objects are realized by the present invention according to which there is provided a process for the synthesis of indene and substituted indenes by the catalytic reaction of substituted and unsubstituted 3-phenylpropionaldehydes and 3-phenylpropylketones, according to the equation:

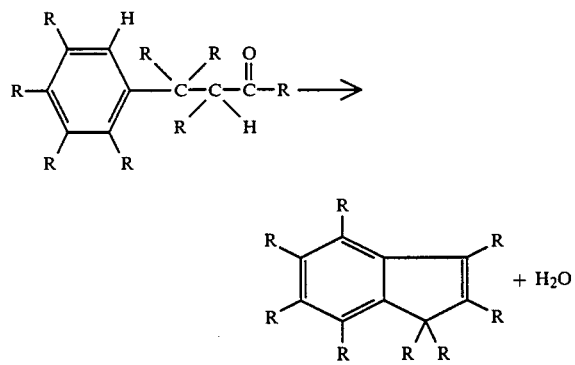

wherein no R group contains ethylenic or acetylenic unsaturation; wherein the R group attached to the carbonyl group is selected from H and hydrocarbyl and each of the remaining R groups is selected independently from hydrogen, halo, nitro, trihalomethyl, acyl, acyloxy, acylthio, lower alkyl secondary amino where each alkyl has 1-4 C atoms, and hydrocarbyl, hydrocarbyloxy and hydrocarbylthio having 1-10 C atoms; wherein hydrocarbyl ring(s) can be formed from one or more adjacent pairs of R groups on the benzene ring; and wherein one of the R groups attached to the benzylic carbon can form a hydrocarbyl ring with the R group attached to the ortho position, said cyclodehydration being effected by passing the starting material aldehyde or ketone in the vapor phase over a solid catalyst which comprises phosphoric acid on a solid inorganic oxide support.

Examples of inorganic oxide supports are silica, silica-alumina and the like. Especially useful is the highly siliceous material, kieselguhr, otherwise known as diatomaceous earth or diatomite.

In the foregoing process the substrate aldehyde or ketone usually has 9-35 C atoms. Of these, a useful group of substrates are those wherein the R groups not on the benzene ring are independently chosen from H and methyl, and in particularly those in which the R groups in the benzene ring are also independently chosen from H and methyl, especially those where such R groups all are H.

Our vapor phase cyclodehydration reaction is effected usually in the temperature range 100°–400° C., more usually in the range 150°–320° C.

Although acid catalyzed cyclizations of 3-phenyl substituted acids or acid derivatives to indanones have been known for many years, subsequent indene formation requires an additional and potentially costly reductive dehydration. An especially attractive alternative, briefly studied nearly a century ago, is the direct formation of indene or a substituted indene by cyclization and subsequent in situ dehydration of 3-phenyl substituted aldehydes or ketones. For example, Miller and Rohde as early as 1892, *Ber.* 1892, 23, 1881–1886, reported a 3.8 percent isolated yield of 1-methylindene from the reaction of 4-phenyl-2butanone (benzylacetone) with a 30-fold molar excess of concentrated sulfuric acid. Under identical conditions, 4-phenyl-3-methyl-2-butanone gave dimethylindene in unspecified yields.

Similarly, 5-amino-2-methylindene was prepared from the reductive cyclization of 3-(m-nitrophenyl)-2-methylpropionaldehyde with zinc and hydrochloric acid at elevated temperatures. Miller W. v. and Kinkelin G. *Ber.* 1886, 19, 1249 and 1520; Miller, W. v. and Rohde, G. ibid 1889, 22, 1830–1843. The difunctional 2-carboxy-4-phenyl-2-butanone reacted with excess sulfuric acid to give an unspecified yield of 1-methyl-2-carboxyindene. Roser, W. *Ber.* 1887, 20, 1574–1576.

These homogenous reactions, using a stoichiometric excesses of liquid acids seem to be the only prior art on this subject, except for recent U.S. Pat. No. 4,568,782, issued Feb. 4, 1986.

In the latter reference the same reaction is catalyzed by a solid Lewis acid as catalyst. However, the reference does not specifically mention the present catalyst, and the results are outstanding with our new catalyst.

The aldehyde and ketone starting materials of the invention can be prepared by well-known methods. For example, linear hydroformylation of styrene and its derivatives yields the corresponding 3-phenylpropionaldehyde (see, for example U.S. Pat. No. 4,052,461 or U.S. Pat. No. 4,268,688 or Lai, R. and Ucciaini, E., *J. Molec. Catal.*, 1978, 4, 401–10; and Cornvil, V. B. and Payer, R., *Chem. Zeitung*, 1974, 98, 596–606.)

In carrying out the process, the aldehyde or ketone is vaporized and passed over the aforementioned solid catalyst, suitably in a fixed bed configuration at temperatures in the range before noted.

A non-reactive carrier vapor or diluent gas such as nitrogen or argon can be used but is not required. When such a diluent is used the concentration of the substrate in the total feed is usually in the range of from 0.001 to 50 volume percent, although higher or lower concentrations can be employed, of course including undiluted substrate vapor. Usual concentration of the substrate is in the range from 0.02 to 20 volume percent. The desired product as well as any unreacted starting materials can be isolated directly from the effluent stream.

Pressures are not critical but usually vary from 1 to 30 psia, more usually 10 to 20 psia.

Contact times used are 0.01–100 sec. usually 0.1–10 sec. (average time for 1 volume of feed to pass over an equal volume of catalyst). Routine experimentation easily reveals optimum contact time for a given set of other conditions.

By the term phosphoric acid it is not intended to specify the exact chemical composition of the phosphorus compound during the course of the reaction under the particular conditions prevailing in the reaction zone. However, it is believed that a significant portion of the phosphorus is present as $H_3PO_4$.

The products of the invention, indene or the defined substituted indenes, have varied uses. All of the products of the present invention are polymerizable to solid thermoplastic polymers useful to mold utilitarian objects, such as tumblers, plates, containers, etc.

The polymerization can be effected using $BF_3$, $TiCl_4$, $SnCl_4$ or $SnCl_5$ as catalysts at low temperatures by the method of Plyusnin, Babin and Chertkova in Zh. Prikl. Khim. 29, 1070 (1956.)

The following specific examples of the invention are merely illustrative and are not to be considered limiting. In effecting the runs of the examples, a stainless steel, fixed-bed downward flow reactor was charged with the particulate solid catalyst and placed in a suitcase furnace set at the desired reaction temperature; a carrier gas or nitrogen was fed through the reactor at the desired rate and the aldehyde or ketone was continuously added at the desired rate. Pressure in the reaction tube was about 0.6 psig. The catalyst was phosphoric acid supported on kieselguhr, made by UOP (designated as SPA-4 catalyst, nominally $H_3PO_4$ on kieselguhr, the amount of the acid being 75 parts acid (expressed as $P_2O_5$) on 25 parts kieselguhr). Products were isolated by passing the effluent stream through ice-cold $CCl_4$. The resulting solution was directly analyzed by gas chromatograph.

Examples 1–6 are shown in Table 1 in tabular form.

TABLE 11

| | | Reaction of 3-phenylbutanal | | |
|---|---|---|---|---|
| Example No. | Temp °C. | Time Secs. | Conversion % | Selectivity to 3-methylindene % | Selectivity to 1-methylinde % |
| 1 | 202 | 0.69 | 96.8 | 40.7 | 43.6 |
| 2 | 203 | 0.35 | 95.8 | 35.6 | 53.6 |
| 3 | 203 | 0.10 | 60.4 | 29.2 | 64.1 |
| 4 | 154 | 0.76 | 93.9 | 11.7 | 72.6 |
| 5 | 253 | 0.63 | 99.3 | 59.4 | 22.7 |
| 6 | 303 | 0.58 | 100 | 64.3 | 14.1 |

The direct product of the reaction in Table 1 is presumably 1-methylindene which can and does isomerize at least in part to 3-methylindene. Thus, in this reaction, 3-phenylbutanal can be converted to 1-methylindene, 3-methylindene, or both.

When it is desired to convert 1-methylindene to 3-methylindene, this is easily done by treatment with base. See J. Org. Chem. 40, 720, 1975.

EXAMPLE 7

A similar run was made except that the substrate feed was benzylacetone, the temperature was 200° C. and the selectivity to 3-methylindene was over 90 percent at about 60 percent conversion.

EXAMPLE 8

When Example 2 is repeated, except that the substrate feed is 3-phenylpropionaldehyde, a good yield and selectivity to indene are obtained.

As will be evident to those skilled in the art various modifications of this invention can be made or followed in the light of the foregoing disclosure and discussion without departing from the spirit and scope of the disclosure or from the scope of the claims.

We claim:

1. A process for the synthesis of indene and substituted indenes by the catalytic reaction of a substrate substituted and unsubstituted 3-phenylpropionaldehydes and 3-phenylpropylketones, according to the equation:

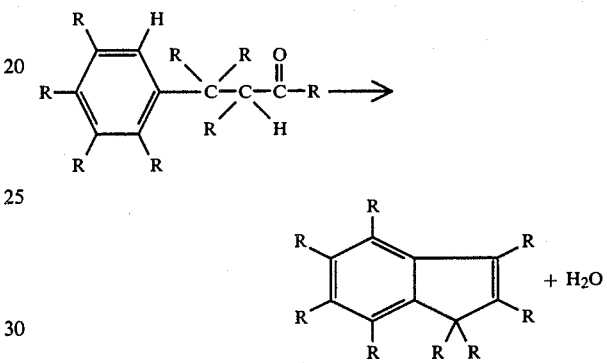

wherein no R group contains ethylenic or acetylenic unsaturation; wherein the R group attached to the carbonyl group is selected from H and hydrocarbyl and each of the remaining R groups is selected independently from hydrogen, halo, nitro, trihalomethyl, acyl, acyloxy, acylthio, lower alkyl secondary amino where each alkyl has 1–4 C atoms, and hydrocarbyl, hydrocarbyloxy and hydrocarbylthio having 1–10 C atoms; wherein hydrocarbyl ring(s) can be formed from one or more adjacent pairs of R groups on the benzene ring; and wherein one of the R groups attached to the benzylic carbon can form a hydrocarbyl ring with the R group attached to the ortho position, said cyclodehydration being effected by passing the starting material aldehyde or ketone in the vapor phase over a solid catalyst which comprises phosphoric acid on a solid inorganic oxide support.

2. A process according to claim 1 wherein said substrate contains 9–35 C atoms.

3. A process according to claim 1 wherein the temperature of the reaction is in the range from 100°–400° C.

4. A process according to claim 1 wherein the temperature of the reaction is in the range from 100°–320° C.

5. A process of claim 4 wherein the contact time is in the range from 0.01–100 seconds.

6. A process of claim 4 wherein the contact time is 0.1–10 seconds.

7. A process according to claim 2 wherein the R groups not on the benzene ring are independently chosen from H and methyl.

8. A process according to claim 7 wherein all R groups on the benzene ring are H.

9. A process according to claim 1 wherein said substrate is 3-phenylbutanal and the product of synthesis is 3-methylindene and/or 1-methylindene.

10. A process of claim 1 wherein said substrate is benzylacetone.

* * * * *